United States Patent
Lee

(10) Patent No.: US 9,511,176 B2
(45) Date of Patent: Dec. 6, 2016

(54) HOMECARE SUCTION DEVICE

(71) Applicant: Wen Ching Lee, Taichung (TW)

(72) Inventor: Wen Ching Lee, Taichung (TW)

(*) Notice: Subject to any disclaimer, the term of this patent is extended or adjusted under 35 U.S.C. 154(b) by 406 days.

(21) Appl. No.: 13/795,166

(22) Filed: Mar. 12, 2013

(65) Prior Publication Data

US 2014/0180205 A1 Jun. 26, 2014

(30) Foreign Application Priority Data

Dec. 21, 2012 (CN) .................. 2012 2 0714977 U

(51) Int. Cl.
*A61M 1/00* (2006.01)
*A61B 17/24* (2006.01)
*A61M 1/06* (2006.01)
*A61M 11/06* (2006.01)
*A61M 15/00* (2006.01)

(52) U.S. Cl.
CPC ............ *A61M 1/0023* (2013.01); *A61B 17/24* (2013.01); *A61B 2017/246* (2013.01); *A61M 1/06* (2013.01); *A61M 11/06* (2013.01); *A61M 15/0021* (2014.02); *A61M 2205/276* (2013.01)

(58) Field of Classification Search
CPC ...... A61M 1/06; A61M 1/0023; A61M 39/12; A61M 11/06; A61M 1/0058; A61M 1/0062; A61M 1/007; A61M 2210/1007; A61B 2017/246; A61B 17/24
USPC ...................................... 285/239, 242, 124.3
See application file for complete search history.

(56) References Cited

U.S. PATENT DOCUMENTS

| 3,084,691 | A | * | 4/1963 | Stoner ................. A61M 1/0023 215/309 |
| 4,229,029 | A | * | 10/1980 | Boyer et al. ................... 285/242 |
| 5,295,957 | A | * | 3/1994 | Aida et al. ....................... 604/74 |
| 6,070,659 | A | * | 6/2000 | Hosoya ......................... 165/178 |
| 2003/0212374 | A1 | * | 11/2003 | Gusler ........................... 604/326 |
| 2005/0251089 | A1 | * | 11/2005 | Lee et al. ......................... 604/74 |
| 2005/0283900 | A1 | * | 12/2005 | Campbell .......................... 4/507 |
| 2007/0135778 | A1 | * | 6/2007 | Murray ............... A61M 1/0001 604/317 |
| 2011/0054389 | A1 | * | 3/2011 | Do ....................... A61M 1/0023 604/28 |

FOREIGN PATENT DOCUMENTS

GB             185521       *  9/1922  .............. A61M 1/06

* cited by examiner

*Primary Examiner* — Theodore Stigell
*Assistant Examiner* — Benjamin Koo
(74) *Attorney, Agent, or Firm* — Rosenberg, Klein & Lee

(57) ABSTRACT

A homecare suction device includes a main body having a housing. An air pump is mounted in the housing and in communication with an air outlet and an air inlet of the housing. A breast pump includes a cover mounted to an opening of a container for receiving a liquid. The cover includes a liquid sucking unit and an air sucking unit. The liquid sucking unit includes a liquid passage and a cup for contacting with an object. The air sucking unit includes an air passage and a connection port in communication with the air inlet of the main body. A funnel is mounted in the cover and in communication with the liquid passage, the air passage, and the interior of the container. The cover further includes a vent communicating the interior of the container with the outside. The air inlet is connected to the connection port by a hose.

5 Claims, 8 Drawing Sheets

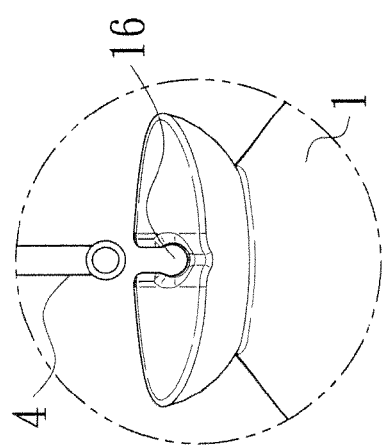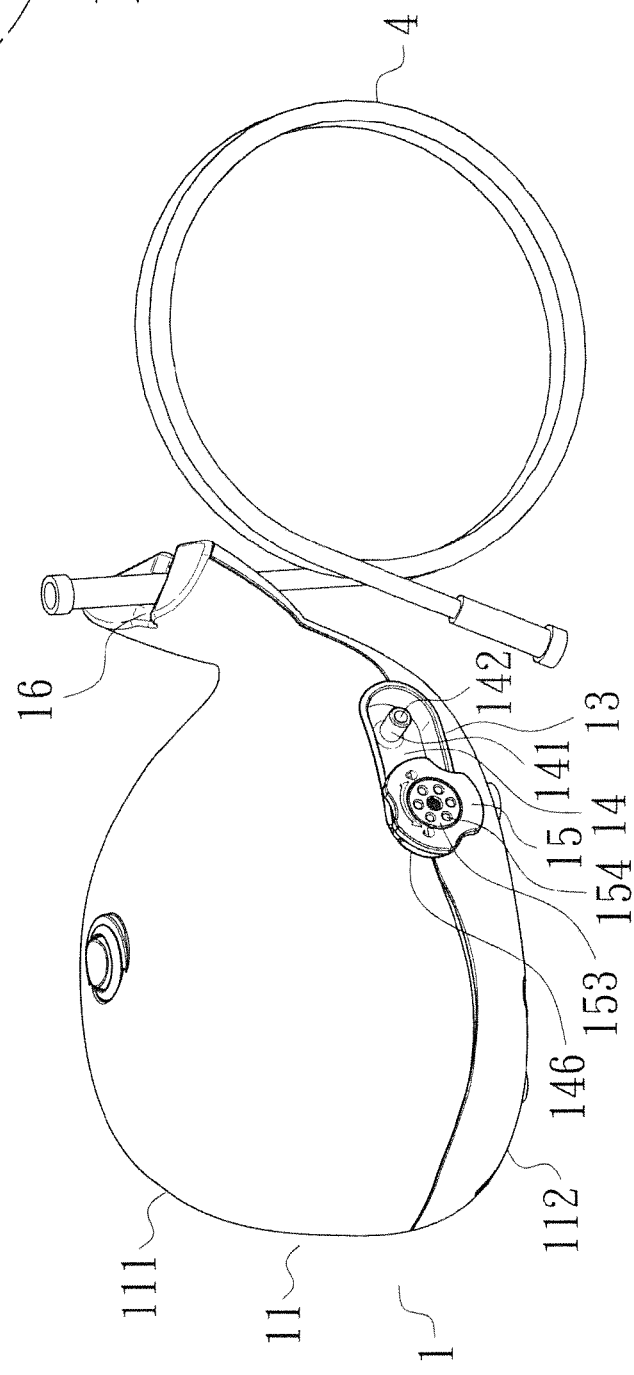

HOMECARE SUCTION DEVICE

BACKGROUND OF THE INVENTION

The present invention relates to a homecare suction device and, more particularly, to a homecare suction device including a main body and a breast pump.

A suction device generally includes a main body having an air inlet or an air outlet for sucking or injecting purposes. The suction device can be used in medical treatments, such as medical care of nasal cavities and throats of patients in ear-nose-throat departments of hospitals and elderly healthcare centers. In an application of the sucking function, a nasal mucus sucker can be used with the main body of the suction device to suck nasal mucus and accumulated phlegm out of the nasal cavity of a patient. In an application of the injecting function, an injector (or nasal spray) can be used with the main body to clean the nasal cavity, the throat or a wound of a patient. In another application of the injecting function, a sprayer can be used with the main body to proceed with spray treatment in the nasal cavity or throat.

In addition to treatment in the nasal cavity or throat using the sucking or injecting function of the suction device, a breast pump for sucking breast milk operates under a suction force. A large space will be occupied if a main body is attached to each of the nasal mucus sucker, the injector, the sprayer, and the breast pump. Thus, a need exists for a novel suction device main body that can be detachably assembled with the nasal mucus sucker, the injector, the sprayer, or the breast pump to reduce the space for storage.

Furthermore, a breast pump is generally connected to a container for receiving breast milk. A negative pressure will be generated in the breast pump and an interior of the container if no ventilation device is provided in the breast pump or the container. The breast milk will be sucked into an air pump in the main body of the suction device if the negative pressure is too large, adversely affecting operation of the air pump and shortening the service life of the main body.

BRIEF SUMMARY OF THE INVENTION

A homecare suction device according to the present invention includes a main body having a housing. An air pump is mounted in the housing. The housing includes an air outlet and an air inlet. The air pump is in communication with the air outlet and the air inlet. A container includes an opening. The container is adapted to receive a liquid. A breast pump includes a cover mounted to the opening of the container. The cover includes a liquid sucking unit and an air sucking unit. Each of the liquid sucking unit and the air sucking unit is in communication with an interior of the container. The liquid sucking unit includes a liquid passage and a cup. The cup is adapted to contact with an object. The air sucking unit includes an air passage and a connection port in communication with the air inlet of the main body. A funnel is mounted in the cover and in communication with the liquid passage, the air passage, and the interior of the container. The cover further includes a vent communicating the interior of the container with the outside, preventing generation of an excessive negative pressure in the container to avoid the liquid in the container from being sucked into the air passage. A hose includes two ends respectively connected to the air inlet and the connection port.

The hose connected between the air inlet and the connection port allows easy detachment of the breast pump from the main body, allowing use of the main body with a device requiring suction, injection, or atomization. Due to provision of the funnel between the cover and the opening of the container, the liquid from the breast pump can flow through the liquid passage and the funnel into the container in which the liquid can be stored. Since the air pump continuously draws air to suck the liquid, a sucking force is applied to the object during operation of the air pump because the air passage is also in communication with the interior of the container via the funnel. Namely, the air in the container is sucked out and generates a negative pressure in the container. When the negative pressure in the container becomes too large, the liquid in the container will be sucked into the air passage via the funnel, causing damage to the air pump. The vent of the cover communicating the interior of the container with the outside avoids excessive negative pressure in the container, avoiding the liquid in the container from entering the air pump via the air passage, maintaining normal operation of the air pump and prolonging the service life of the air pump.

The present invention will become clearer in light of the following detailed description of illustrative embodiments of this invention described in connection with the drawings.

DESCRIPTION OF THE DRAWINGS

FIG. 4 shows a perspective view of the main body and a hose.

FIG. 4A is an enlarged view of a portion of the main body and an end of the hose.

DETAILED DESCRIPTION OF THE INVENTION

Figure 1:
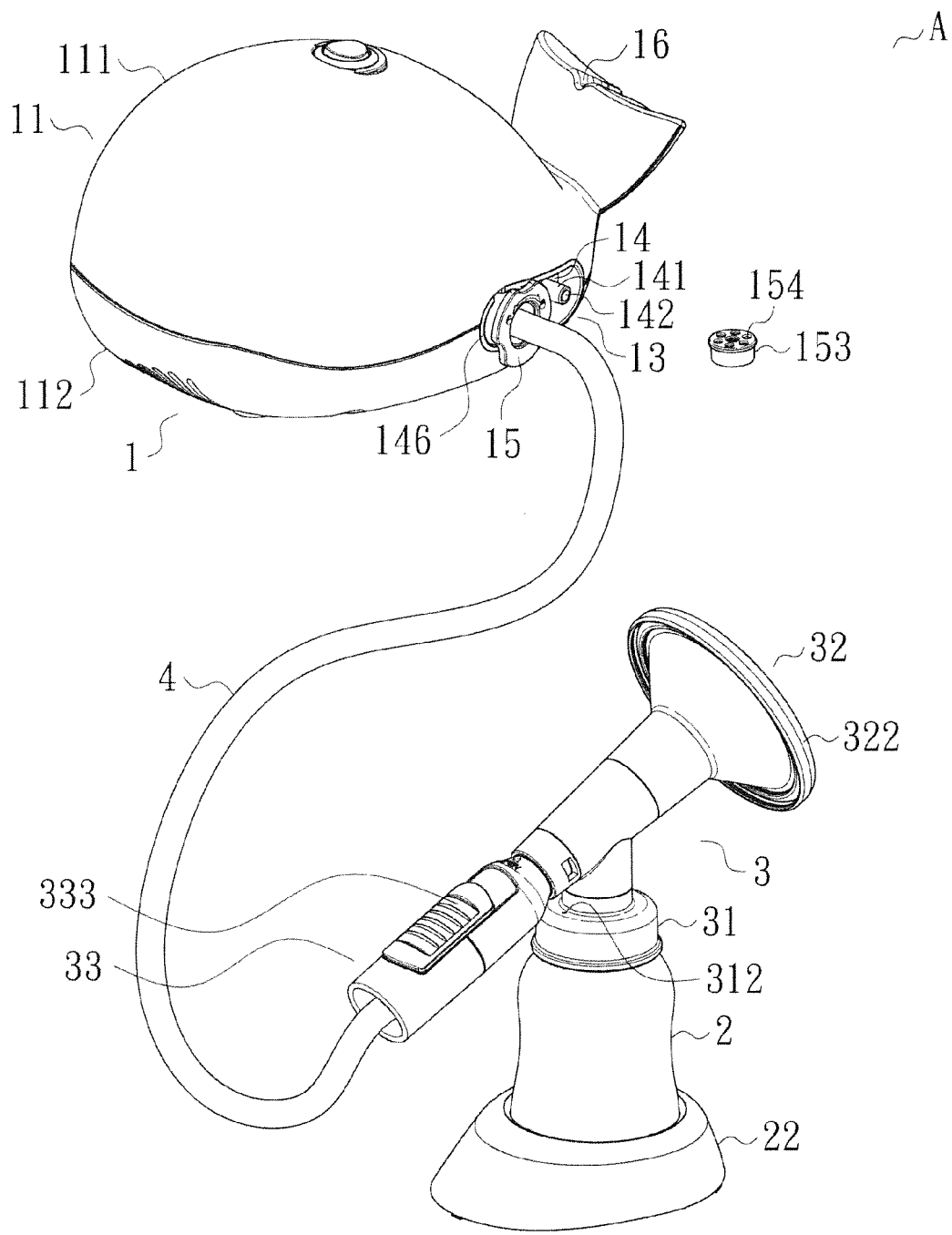
FIG. 1 shows a perspective view of a homecare suction device according to the present invention.
Figure 2:
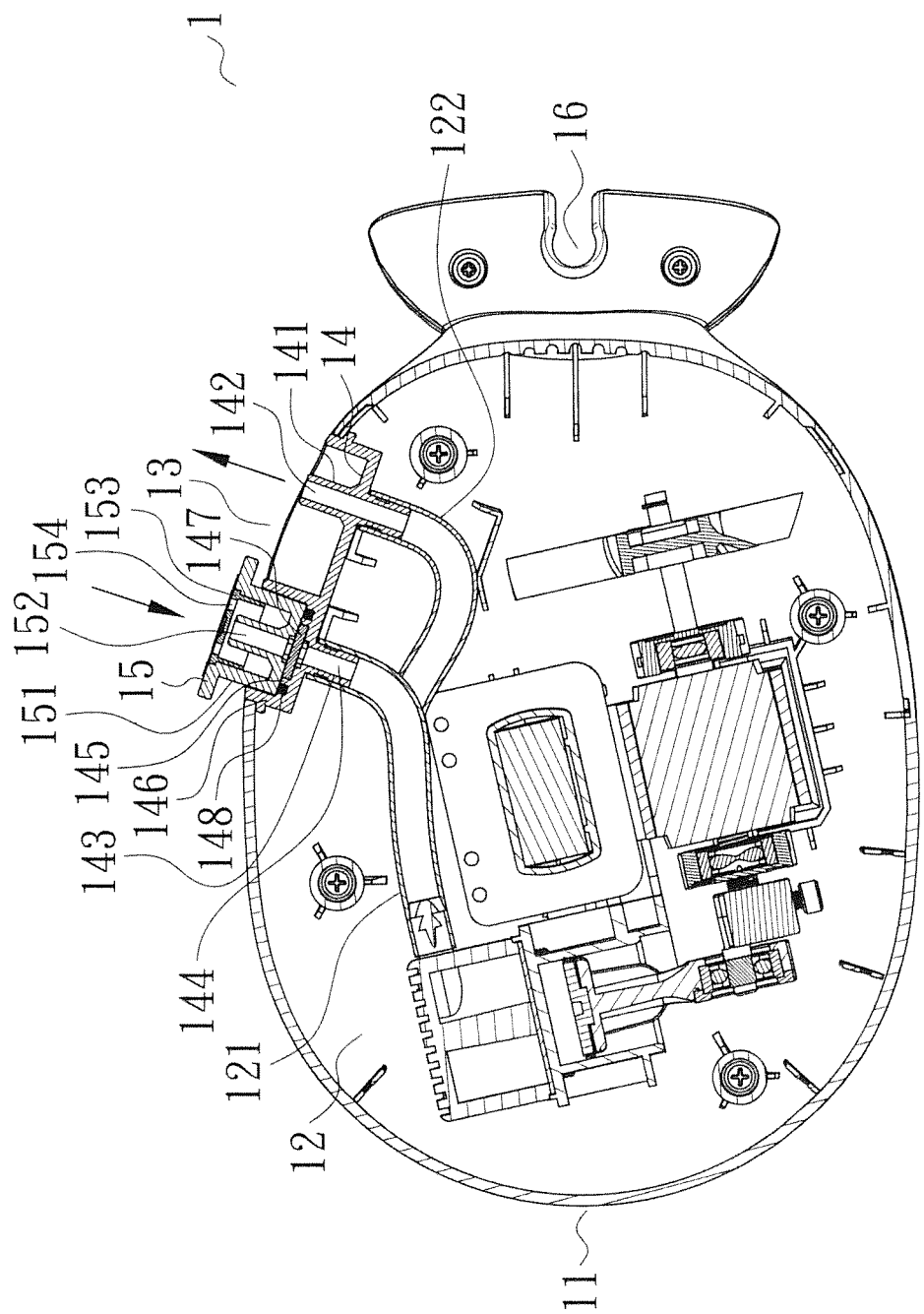
FIG. 2 shows a cross sectional view of a main body of the homecare suction device according to the present invention.
Figure 3:
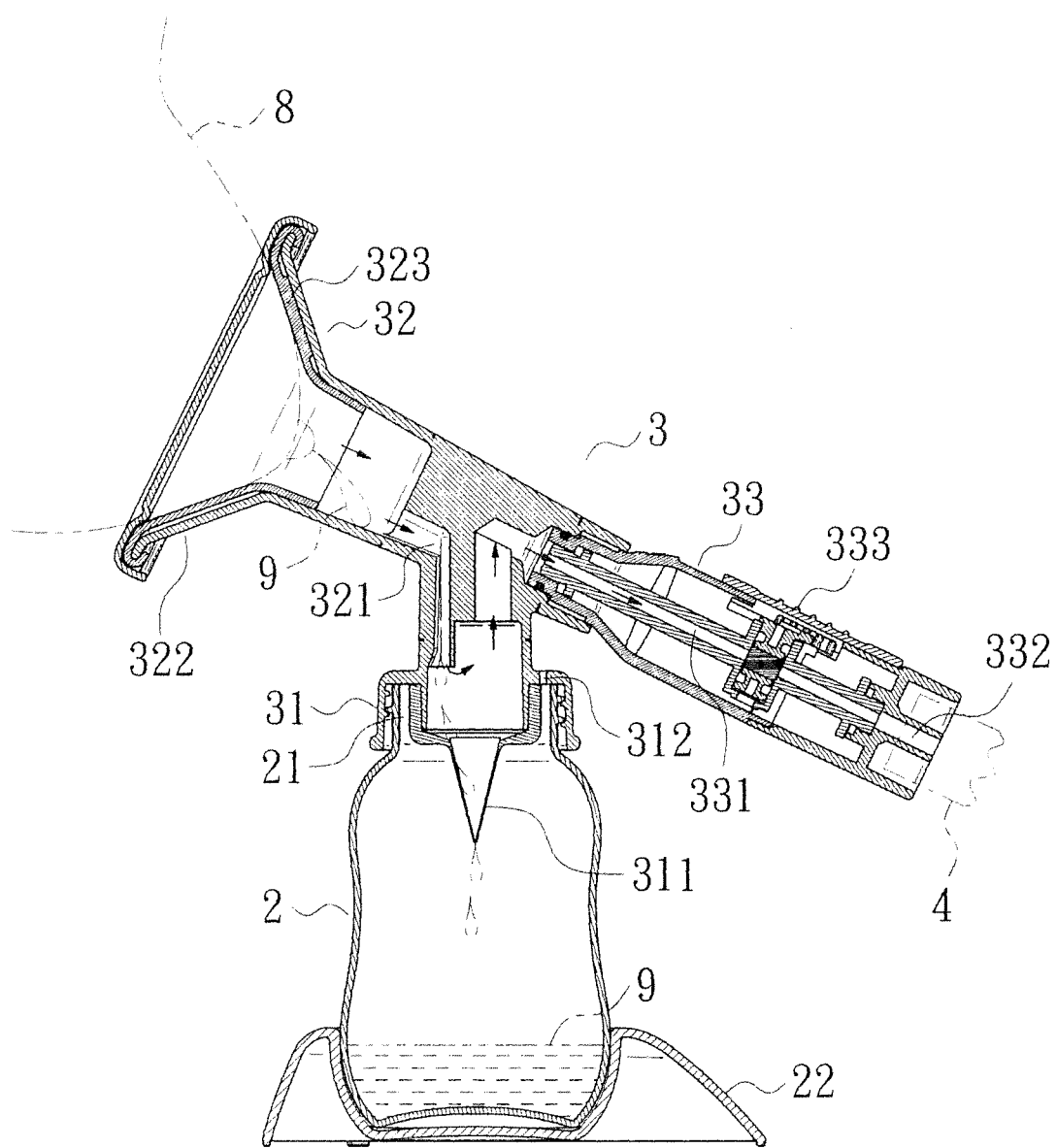
FIG. 3 shows a cross sectional view of a breast pump and a container.

With reference to FIGS. 1-3, a homecare suction device A according to the present invention includes a main body 1 having a housing 11. An air pump 12 is mounted in the housing 11. The housing 11 includes an air outlet 142 and an air inlet 144. The air pump 12 is in communication with the air outlet 142 and the air inlet 144.

The homecare suction device A further includes a container 2 having an opening 21. The container 2 is adapted to receive a liquid 9. In the preferred embodiment, the container 2 is supported on a base 22.

The homecare suction device A further includes a breast pump 3 having a cover 31 mounted to the opening 21 of the container 2. In the preferred embodiment, the cover 31 and the opening 21 of the container 2 are connected by threading connection. The cover 31 includes a liquid sucking unit 32 and an air sucking unit 33. Each of the liquid sucking unit 32 and the air sucking unit 33 is in communication with an interior of the container 2. The liquid sucking unit 32 includes a liquid passage 321 and a cup 322. The cup 322 is adapted to contact with an object 8. In the preferred embodiment, the liquid sucking unit 32 is trumpet-shaped, and a soft rubber pad 323 is mounted to a surface of the cup 322. The air sucking unit 33 includes an air passage 331 and a connection port 332 in communication with the air inlet 144 of the main body 1. In the preferred embodiment, the air sucking unit 33 further includes a control switch 333 for controlling a suction force of the air sucking unit 33, which is known in the art. A funnel 311 is mounted in the cover 31 and in communication with the liquid passage 321, the air passage 331, and the interior of the container 2. In the preferred embodiment, the funnel 311 tapers downward and is located between the cover 31 and the opening 21 of the container 2. The funnel 311 is made of soft rubber. The cover 31 further includes a vent 312 communicating the interior of the container 2 with the outside, preventing generation of an excessive negative pressure in the container 2 to avoid the liquid 9 in the container 2 from being sucked into the air passage 331.

The homecare suction device A further includes a hose 4 having two ends respectively connected to the air inlet 144 and the connection port 332. Thus, the main body 1 and the breast pump 3 can be easily detached from each other, allowing use of the main body 1 with a device requiring suction, injection, or atomization.

Figure 5:
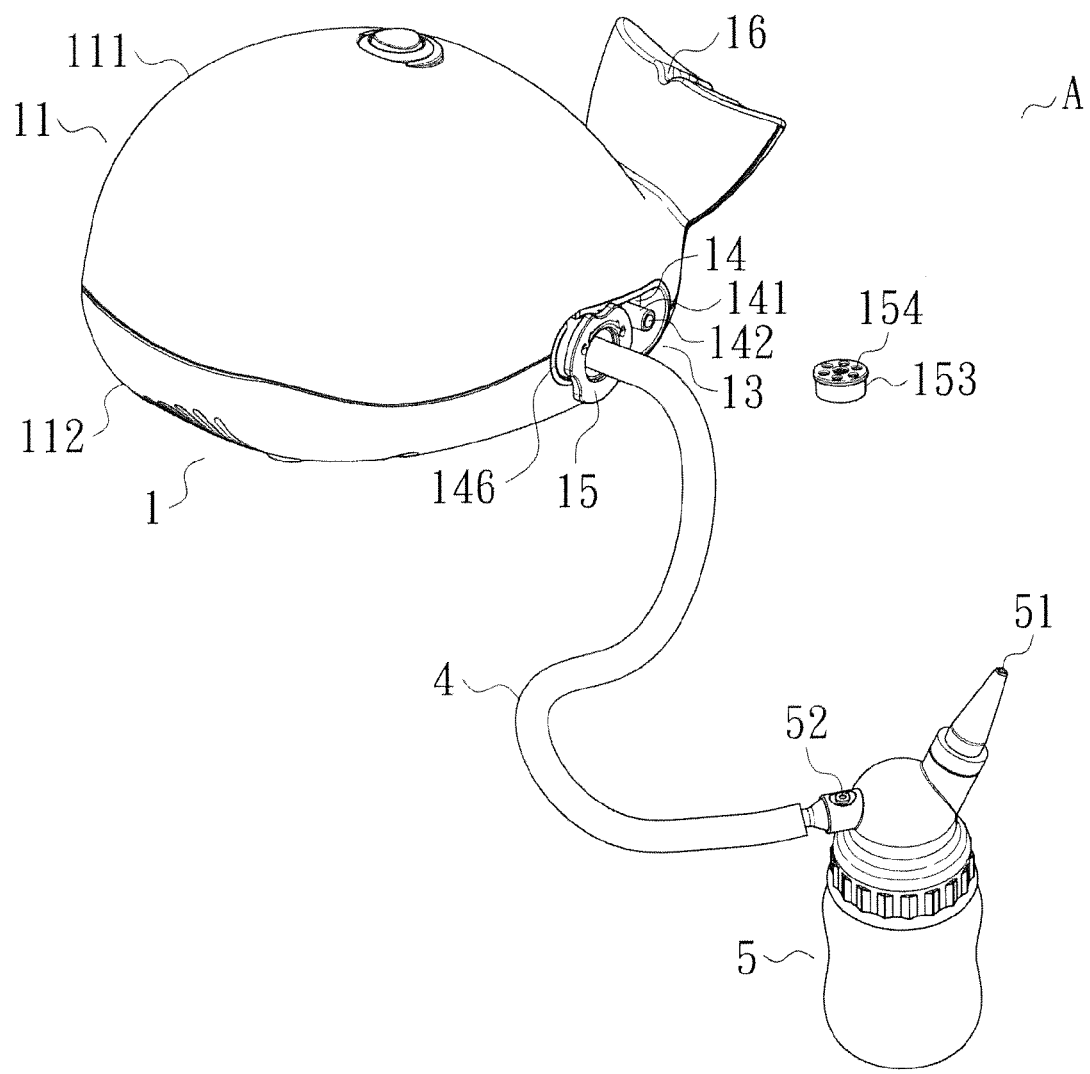
FIG. 5 shows a perspective view of the main body and a nasal mucus sucker.
Figure 6:
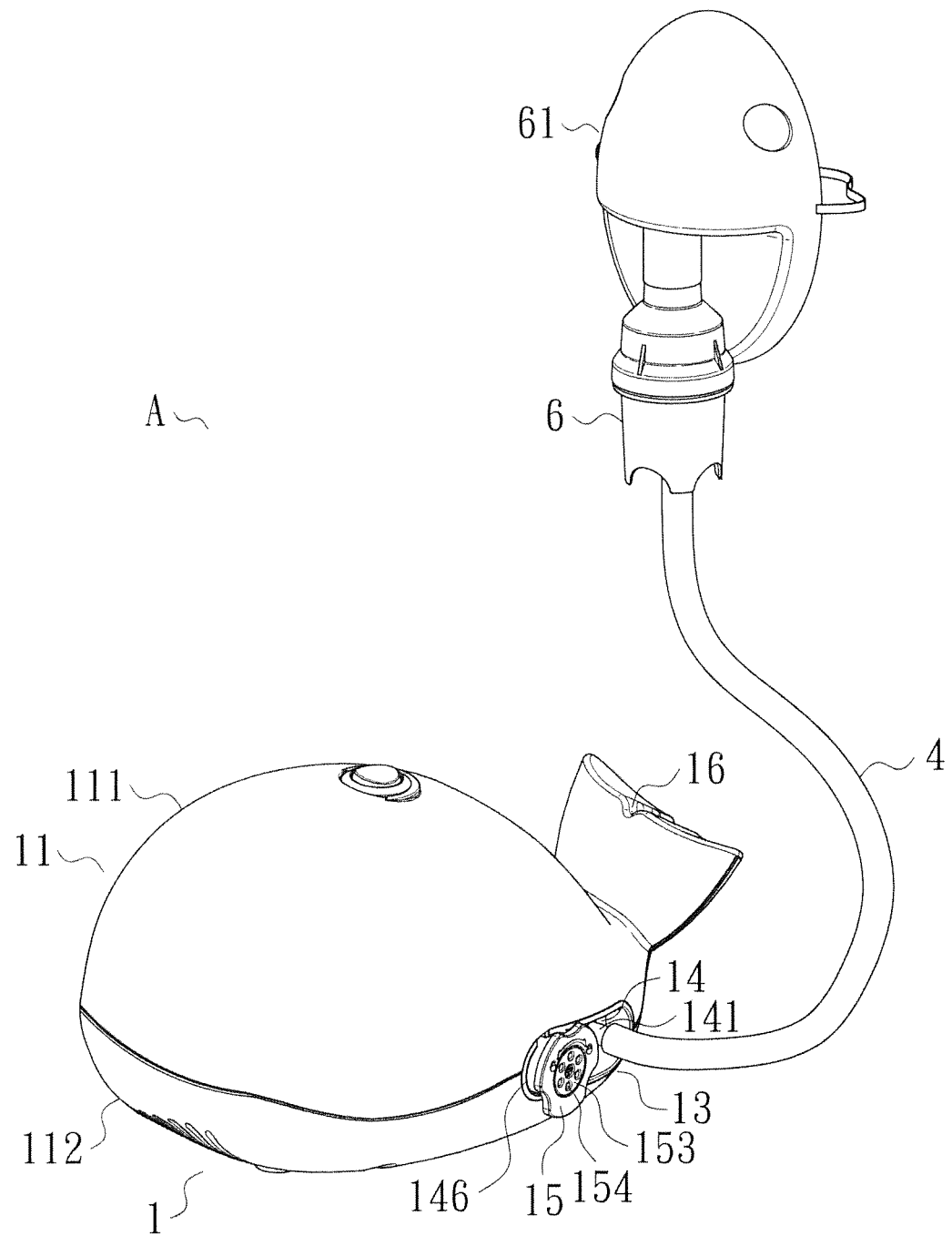
FIG. 6 shows a perspective view of the main body and a sprayer with a mask.
Figure 7:
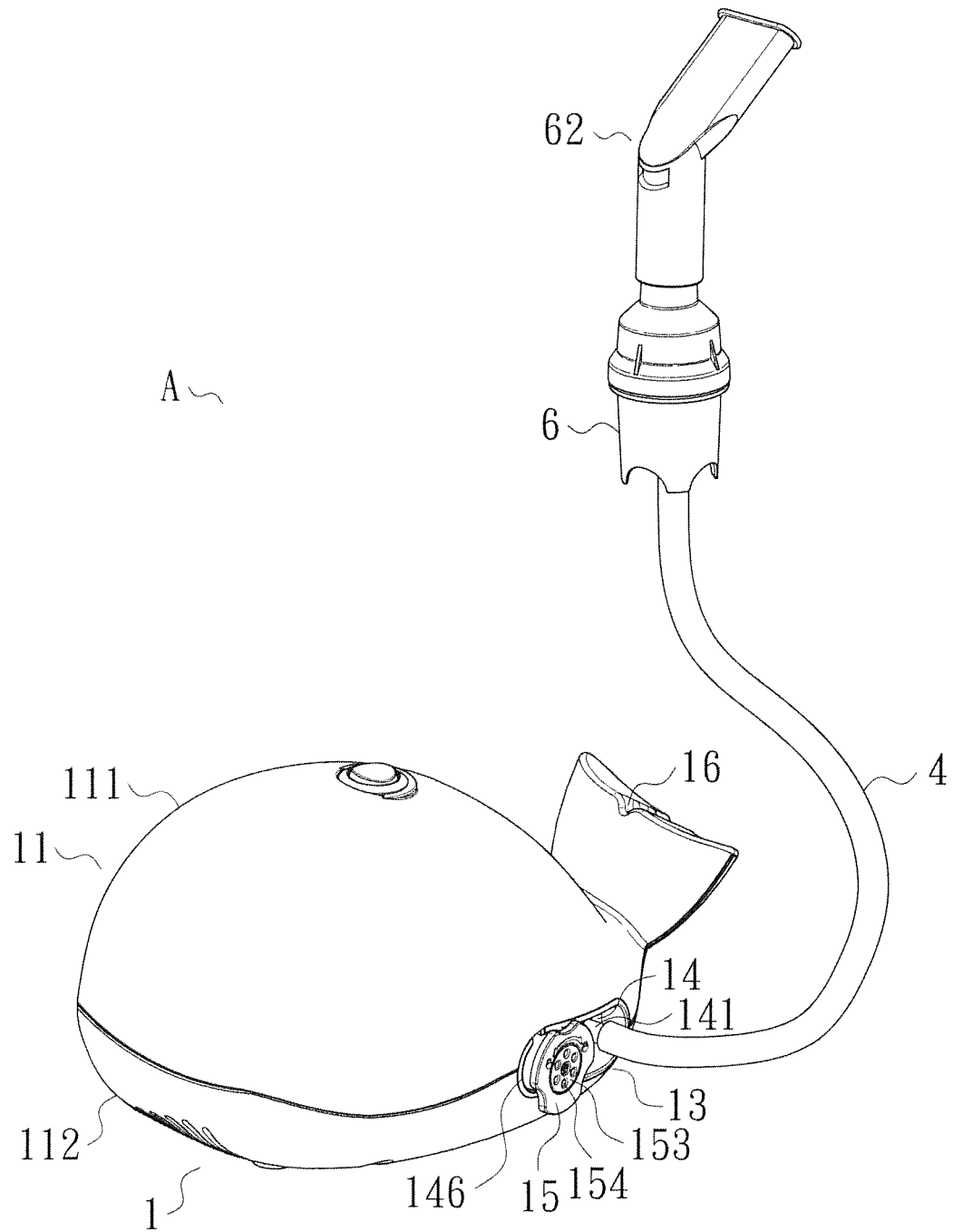
FIG. 7 shows a perspective view of the main body and a sprayer with a mouth biting portion.
Figure 8:
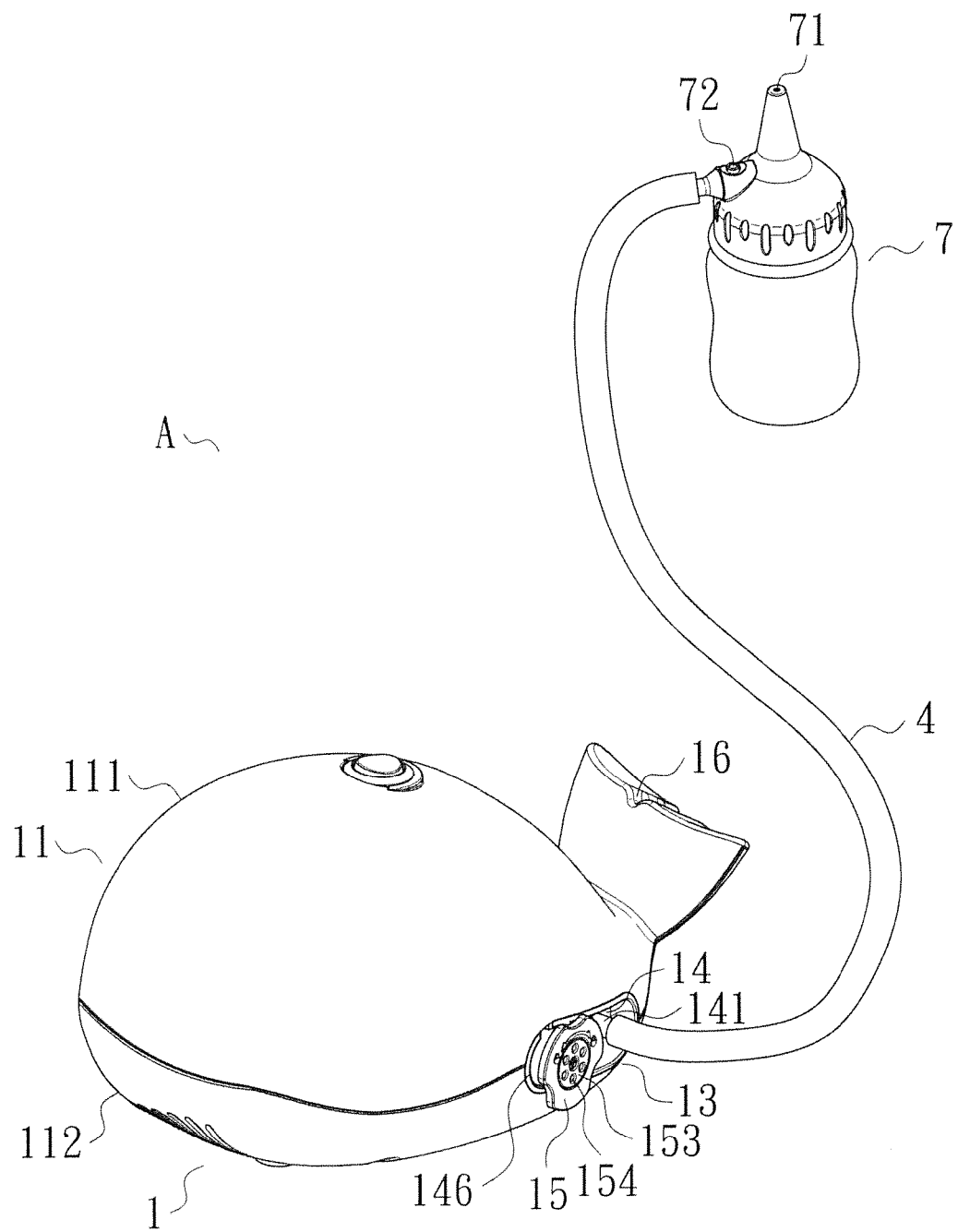
FIG. 8 shows a perspective view of the main body and an injector.

In an embodiment shown in FIG. 5, the air inlet 144 is connected by the hose 4 to a nasal mucus sucker 5. The nasal mucus sucker 5 includes a nasal suction tube 51 and a control hole 52. In another embodiment shown in FIG. 6, the air inlet 144 is connected by the hose 4 to a sprayer 6 with a mask 61 for medical treatment of a nasal cavity of a patient. In a further embodiment shown in FIG. 7, the air inlet 144 is connected by the hose 4 to a sprayer 6 with a mouth-biting portion 62 for medical treatment of a throat of a patient. In still another embodiment shown in FIG. 8, the air inlet 144 is connected by the hose 4 to an injector 7 including an injection tube 71 and a control hole 72. Thus, the main body 1 provides many applications. Use of the nasal mucus sucker 5, the sprayer 6, and the injector 7 are well known in the art and, therefore, not described to avoid redundancy.

Since the funnel 311 is in communication with the liquid passage 321, the air passage 331, and the container 2, the liquid 9 from the breast pump 3 can flow through the liquid passage 321 and the funnel 311 into the container 2 in which the liquid 9 can be stored. Since the air pump 12 continuously draws air to suck the liquid 9, a sucking force is applied to the object 8 during operation of the air pump 12 because the air passage 331 is also in communication with the interior of the container 2 via the funnel 311. Namely, the air in the container 2 is sucked out and generates a negative pressure in the container 2. When the negative pressure in the container 2 becomes too large, the liquid 9 in the container 2 will be sucked into the air passage 331 via the funnel 311, causing damage to the air pump 12. The vent 312 of the cover 31 communicating the interior of the container 2 with the outside avoids excessive negative pressure in the container 2, avoiding the liquid 9 in the container 2 from entering the air pump 12 via the air passage 331, maintaining normal operation of the air pump 12 and prolonging the service life of the air pump 12.

With reference to FIGS. 1, 2, 4A, and 5, the housing 11 includes an upper housing 111, a lower housing 112, and a connection portion 13 sandwiched between the upper and lower housings 111 and 112. The connection portion 13 includes a board 14. An air outlet tube 141 and a first air inlet tube 143 extend through the board 14. The air outlet tube 141 includes the air outlet 142. The first air inlet tube 143 includes the air inlet 144. An annular flange 145 is formed around a top end of the first air inlet tube 143. An annular wall 146 is formed around the annular flange 145. An annular groove is defined between the annular flange 145 and the annular wall 146. Filter cotton 147 is mounted in the annular flange 145 and covers the top end of the first air inlet tube 143. A seal ring 148 is mounted in the annular groove. An inlet coupler 15 is mounted in the annular wall 146. The inlet coupler 15 includes a second air inlet tube 152 and an annular outer wall 151 surrounding the second air inlet tube 152. The second air inlet tube 152 is in communication with the first air inlet tube 143.

Air is filtered by the filter cotton 147 before entering the air pump 12, avoiding accumulation of dirt or bacteria and keeping the air inlet tube 121 clean. Since the filter cotton 147 is mounted to the connection portion 13, replacement of the filter cotton 147 can be easily achieved after detaching the inlet coupler 15.

With reference to FIGS. 2, 4, and 6-8, an air cap 153 is provided to avoid a attachment of a hose to the second air inlet tube 152 or the air outlet tube 141. The air cap 153 is tightly mounted to the second air inlet tube 152 and located in the annular outer wall 151. The air cap 153 includes a top face having an air passageway 154. The air passageway 154 has an inner diameter smaller than an outer diameter of the hose 4. When the user intends to use the air outlet tube 141, the hose 4 is not be attached to the second air inlet 152, in order to avoid adversely affecting the normal operation of the air pump 12 and shortening the service life of the main body 1. With reference to FIGS. 1 and 5, when it is intended to use the second inlet tube 152, the air cap 153 is removed, and the hose 4 is connected to the second inlet tube 152.

With reference to FIG. 4A, the housing 11 includes a fixing hole 16 in an end thereof. The hose 4 can be fixed in the fixing hole 16 when not in use.

Although specific embodiments have been illustrated and described, numerous modifications and variations are still possible without departing from the scope of the invention. The scope of the invention is limited by the accompanying claims.

The invention claimed is:

1. A homecare suction device comprising:
a main body including a housing having an annular wall coupled to an outer surface of said housing, said housing further including an inlet coupler coupled to said annular wall, an air pump mounted in the housing, the housing including an air outlet and an air inlet, the air pump being in communication with the air outlet and the air inlet, the main body being operable to drive a plurality of devices of different types modularly coupled thereto;
one of the modularly coupled devices being a nasal mucus sucker detachably coupled to the main body by a hose, said hose being coupled on opposing ends to said mucus sucker and said inlet coupler, the nasal mucus sucker having a container portion and a connection port; and,
the hose and an air cap adapted to be releasably coupled to the air inlet, the hose including two ends respectively connected in releasable manner to the air inlet and the connection port.

2. The homecare suction device as claimed in claim 1, with the housing including an upper housing, a lower housing, and a connection portion sandwiched between the upper and lower housings, with the connection portion including a board, with an air outlet tube and a first air inlet tube extending from the board, with the air outlet tube including the air outlet, with the first air inlet tube including the air inlet, with an annular flange formed around a top end of the first air inlet tube, with the annular wall formed around the annular flange, with an annular groove defined between the annular flange and the annular wall, with filter cotton mounted in the annular flange and covering the top end of the first air inlet tube, with a seal ring mounted in the annular groove, with the inlet coupler mounted in the annular wall, with the inlet coupler including a second air inlet tube and an annular outer wall surrounding the second air inlet tube, with the second air inlet tube being in communication with the first air inlet tube.

3. The homecare suction device as claimed in claim 2, wherein the air cap is configured to be tightly mounted to the inlet coupler and received in the annular outer wall as an alternative to the hose, the air cap including a top face having a plurality of air passageways formed therein, each of the air passageways having an inner diameter smaller than an outer diameter of the hose.

4. The homecare suction device as claimed in claim 1, with the housing including a fixing hole in an end thereof, with the hose adapted to be fixed in the fixing hole.

5. The homecare suction device as claimed in claim 1, with the air outlet adapted to be selectively connected to a sprayer or an injector by the hose.

* * * * *